United States Patent
Dumler

[19]

[11] Patent Number: 5,974,618
[45] Date of Patent: Nov. 2, 1999

[54] INTERDENTAL CLEANING DEVICE

[75] Inventor: Norbert Dumler, Ansbach, Germany

[73] Assignee: Georg Karl geka-brush GmbH, Bechhofen-Waizendorf, Germany

[21] Appl. No.: 09/017,686

[22] Filed: Feb. 3, 1998

[30] Foreign Application Priority Data

Feb. 18, 1997 [DE] Germany .......................... 197 06 198

[51] Int. Cl.⁶ ................................ A46B 3/18; A46B 9/04
[52] U.S. Cl. ............................. 15/167.1; 15/172; 15/184
[58] Field of Search ................................. 15/167.1, 172, 15/184, 185, 206

[56] References Cited

U.S. PATENT DOCUMENTS

| | | | |
|---|---|---|---|
| 541,727 | 6/1895 | Dennis | 15/172 |
| 1,121,082 | 12/1914 | Farrar | 15/184 X |
| 2,112,658 | 3/1938 | Rathbun | 15/167.1 X |
| 2,395,245 | 2/1946 | Booharin | 15/172 X |
| 2,427,411 | 9/1947 | Krueger | 15/172 |
| 2,749,567 | 6/1956 | Kreuger | 15/172 |
| 4,796,325 | 1/1989 | Bortman | 15/172 X |

FOREIGN PATENT DOCUMENTS

| | | |
|---|---|---|
| 296 01 661 | 5/1996 | Germany . |
| 204205 | 7/1939 | Switzerland ............... 15/172 |

*Primary Examiner*—Mark Spisich
*Attorney, Agent, or Firm*—Browdy and Neimark

[57] ABSTRACT

In an interdental cleaning device comprising a brush and a holder, the brush being pivotably and replaceably disposed on the free end of the holder, and the holder consisting of two shells, it is provided with a view to advantageous pivotablility of the brush and defined stop positions being attained, accompanied with simple implementation in terms of plastics technology, that the brush comprises a ball of a ball and socket joint and that a socket of a ball and socket joint is formed by two socket members to be assembled and disassembled, one socket member at a time being formed on an end of a shell.

19 Claims, 2 Drawing Sheets

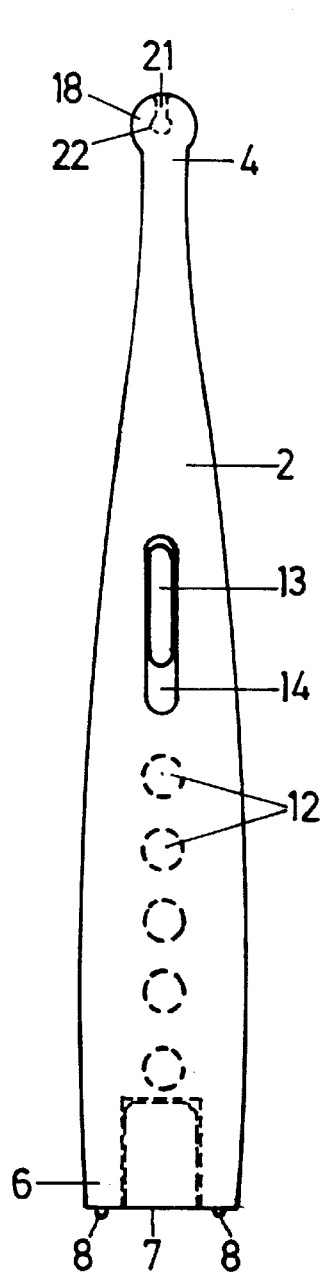
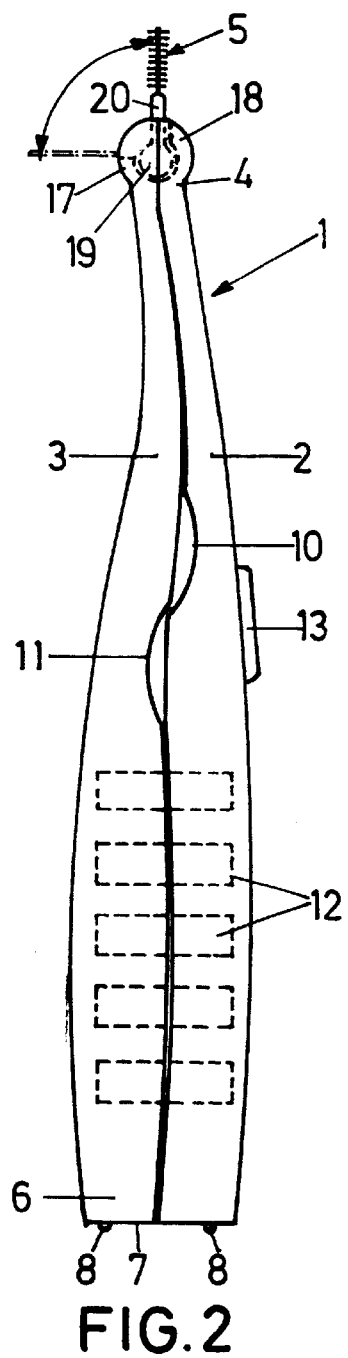
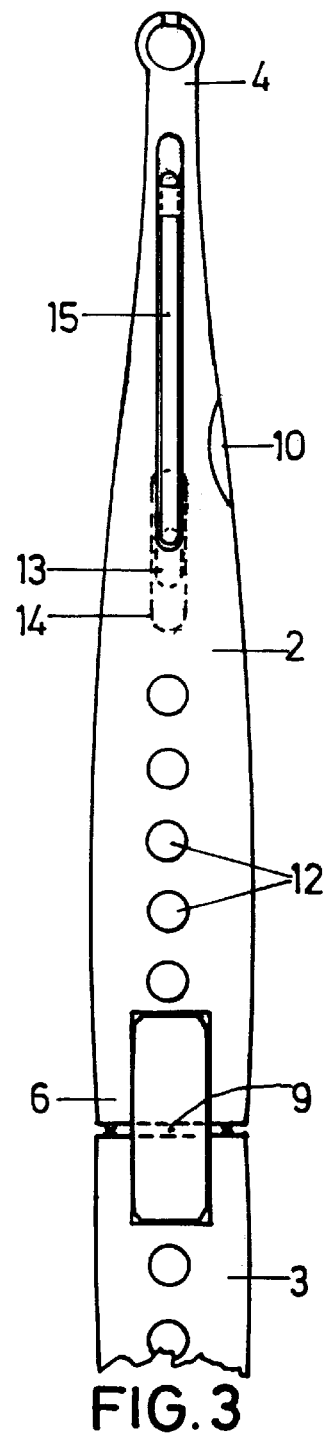

_5,974,618_

INTERDENTAL CLEANING DEVICE

BACKGROUND OF THE INVENTION

1. Field of the Invention

The invention relates to an interdental cleaning device comprising a brush and a holder, the brush being pivotably and replaceably disposed on the free end of the holder, and the holder consisting of two shells.

2. Background Art

A cleaning device of the generic type is known for instance from DE-U296 01 661.

In order for the brush to be pivotable in relation to the holder comparatively easily on the one hand, and having stable stop positions on the other hand so that the respective angle desired for the cleaning operation can be set between the brush and the holder, comparatively high demands are put on the bedding of the brush.

SUMMARY OF THE INVENTION

It is the object of the invention to embody an interdental cleaning device of the type mentioned at the outset in such a way that the pivot bearing of the brush exhibits optimal properties of use on the one hand and that simple implementation in terms of plastics technology is ensured on the other hand.

According to the invention, this object is attained by the brush comprising a ball of a ball and socket joint and by the socket of the ball and socket joint being formed by two socket members to be assembled and disassembled, one socket member at a time being formed on an end of a shell.

The design as a ball and socket joint ensures that friction and stop position stability can be defined and set highly accurately. However, problems are posed by putting into practice the spherical bearings by injection molding since the possibilities of implementing rear recesses are restricted, depending on the plastic materials selected. By appending the socket members to the shells, it is feasible to join the two socket members very tightly to each other without any restriction on the selection of material and the geometry of rear recesses. In this way, it is even possible to use transparent materials that are, however, comparatively brittle such as polystyrene, SAM, PEC, K resin, polycarbonate, or acrylic glass.

In keeping with another embodiment of the invention, a locking mechanism is provided, interlocking the shells in their closed condition. In this way, it is possible to render the interior space between the shells optionally accessible and there to accommodate for instance spare brushes for replacement after wear or brushes having a different top for certain cleaning purposes.

By advantage, the locking mechanism may comprise a slide and a lengthwise displaceable locking member joined to the latter on a first shell of the holder, and an arresting member, into which to push the locking member, on the second shell of the holder.

For pivoting of the brush to be possible on the one hand and for the brush to be secured in a direction perpendicular to the pivoting direction and the stop positions to be stabilized, at least one of the socket members of the ball and socket joint may have a slit with locking recesses which surrounds the stem of the brush.

At their ends turned away from the brush, the two shells of the holder may be united by a hinge, in particular an integral hinge.

The end of the holder that is turned away from the brush may have a base so that it is possible to place such an interdental cleaning device in a toilet cabinet or the like, thus saving space.

In order to obtain reliable upright standing, legs may be formed on the base in the form of knob-type elevations.

For simplification of the opening of the two shells, at least one of them can be provided with a recessed grip that stands back from the inner edge.

Details of the invention will become apparent from the ensuing description of a preferred exemplary embodiment, taken in conjunction with the drawing.

BRIEF DESCRIPTION OF THE DRAWING

FIG. 1 is a view of an interdental cleaning device according to the invention,

FIG. 2 is a view rotated by 90° as compared with FIG. 1, illustrating the pivotability of the brush, FIG. 3 is a view partially broken off of the interdental cleaning device in an unfolded condition.

DESCRIPTION OF THE PREFERRED EMBODIMENT

Figure 4:
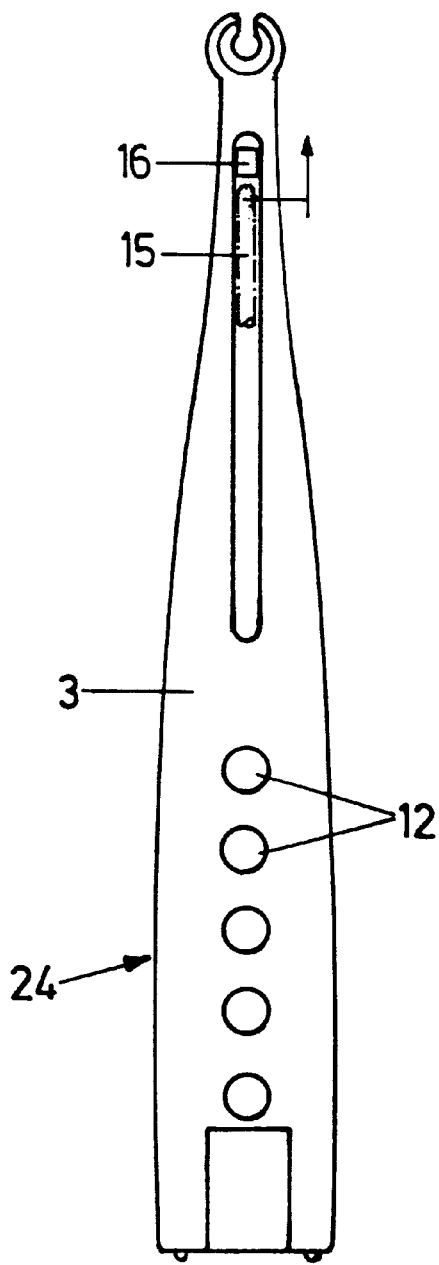
FIG. 4 is a view, in the unfolded condition, of the shell seen in FIG. 1 from an angle of view rotated by 180°.
Figure 5:
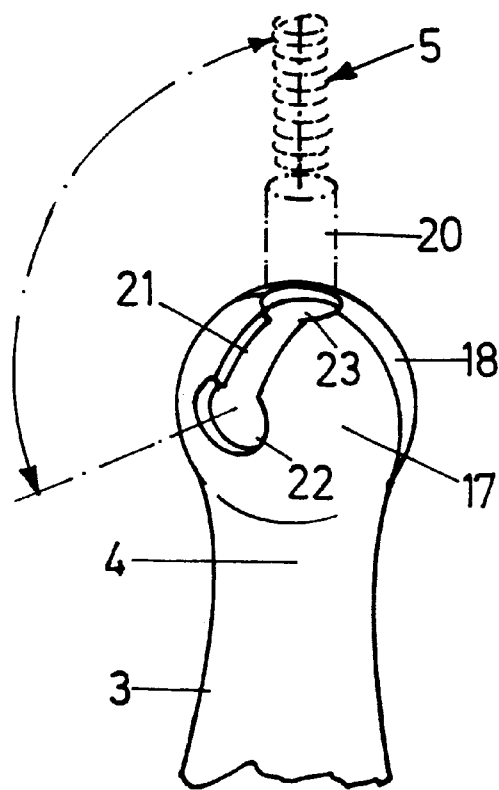
FIG. 5 is a perspective, enlarged view of the bearing portion of the brush.

An interdental cleaning device 1 seen in the drawing comprises two shells 2, 3, on one end 4 of which a brush 5 is pivotably mounted, and the other end 6 of which is configured as a base 7 with legs 8, the shells 2, 3 being connected with each other in a manner to be flexibly unfoldable by way of an integral hinge 9. For simplification of the unfolding operation, recessed grips 10, 11 are provided on each of the shells. As roughly outlined housings 12 permit further brushes to be housed inside the shells 2, 3.

For interlocking the two shells 2, 3, a slide 13 is provided, which is positioned for lengthwise displacement in a longitudinal recess 14 of the shell 2. On its underside, i.e. on the inside of the shell 2, the slide 13 is joined to a locking member 15 which may be formed by an elastic bar of plastic material guided lengthwise. An arresting member 16 is mounted on the other shell 3, having the shape of an eyelet into which to push the locking member 15 for interlocking.

As seen in particular from FIG. 2 in combination with FIG. 4, a hemispherical socket member 17, 18 is molded on the end 4, on the side of the brush, of each shell 2, 3 so that a spherical bearing recess is produced inside, which comprises a ball 19 of a ball and socket joint, the stem 20 of the brush 5 being fixed to this ball 19. A slit 21 is formed in the socket member 17, extending over an angle of approximately 90° and at the ends of which recesses 22, 23 are formed, the diameter of which corresponds approximately to the diameter of the stem 20, whereas the width of the slit 21 is smaller than the diameter of the stem 20, two stable stop positions for the brush thus being defined, namely in axial prolongation of the holder 24 formed by the shells 2, 3 on the one hand and perpendicular thereto on the other.

What is claimed is:

1. An interdental cleaning device comprising a brush and a holder, the brush being pivotably and replaceably disposed on a first end of the holder, and the holder consisting of two shells, wherein the brush (5) comprises a ball (19) of a ball and socket joint and wherein a socket of the ball and socket joint is formed by two half socket members (17, 18) which when assembled form the socket, the two half socket members each respectively formed on a first end of each shell (2, 3) of the two shells of the holder (24);

wherein the two shells (2, 3) are united by an integral hinge (9) engaged to a second end (6) of each shell of the two shells and each said second end is spaced away from the brush (5) to form a distal end of the holder.

2. An interdental cleaning device according to claim 1, wherein a locking mechanism is provided for interlocking the two shells (2, 3) in a closed condition.

3. An interdental cleaning device according to claim 2, wherein the locking mechanism comprises a slide (13) and a lengthwise displaceable locking member (15) joined to the slide (13) on a first shell (2, 3) of said two shells and an arresting member (16) on a second shell (2, 3) of said two shells into which the locking member can be pushed.

4. An interdental cleaning device according to claim 10, wherein at least one of the two half socket members (17, 18) of the ball and socket joint has a slit (21) with locking recesses (22, 23) within which the brush is slidably engaged.

5. An interdental cleaning device according to claim 1, wherein at least one cavity (12) is formed in an interior space between the two shells (2, 3) for accommodation of a brush.

6. An interdental cleaning device according to claim 1, wherein the distal end of the holder (24) has a base (7).

7. An interdental cleaning device according to claim 6, wherein knob-type legs (8) are disposed on the base (7).

8. An interdental cleaning device according to claim 6, wherein a recessed grip (10, 11) is formed away from an inner edge on at least one of the two shells (2, 3).

9. An interdental cleaning device comprising a brush and a holder, the brush being pivotably and replaceably disposed on a first end of the holder, and the holder consisting of two shells, wherein the brush (5) comprises a ball (19) of a ball and socket joint and wherein a socket of the ball and socket joint is formed by two half socket members (17, 18) which when assembled form the socket, the two half socket members each respectively formed on a first end of each shell (2, 3) of the two shells of the holder (24);

wherein a locking mechanism is provided for interlocking the two shells (2, 3) in a closed position;

wherein the locking mechanism comprises a slide (13) and a lengthwise displaceable locking member (15) joined to the slide (13) on a first shell (2, 3) of said two shells and an arresting member (16) on a second shell (2, 3) of said two shells into which the locking member can be pushed.

10. An interdental cleaning device according to claim 9 wherein at least one cavity (12) is formed in an interior space between the two shells (2, 3) for accommodation of a brush.

11. An interdental cleaning device according to claim 9, wherein the distal end of the holder (24) has a base (7).

12. An interdental cleaning device according to claim 11, wherein knob-type legs (8) are disposed on the base (7).

13. An interdental cleaning device according to claim 9, wherein a recessed grip (10, 11) is formed away from an inner edge on at least one of the two shells (2, 3).

14. An interdental cleaning device comprising a brush and a holder, the brush being pivotably and replaceably disposed on a first end of the holder, and the holder consisting of two shells, wherein the brush (5) comprises a ball (19) of a ball and socket joint and wherein a socket of the ball and socket joint is formed by two half socket members (17, 18) which when assembled form the socket, the two half socket members each respectively formed on a first end of each shell (2, 3) of the two shells of the holder (24);

wherein at least one of the two half socket members (17, 18) of the ball and socket joint has a slit (21) with locking recesses (22, 23) within which the brush is slidably engaged.

15. An interdental cleaning device according to claim 14, wherein a locking mechanism is provided for interlocking the two shells (2, 3) in a closed condition.

16. An interdental cleaning device according to claim 14, wherein at least one cavity (12) is formed in an interior space between the two shells (2, 3) for accommodation of a brush.

17. An interdental cleaning device according to claim 14, wherein the distal end (6) of the holder (24) has a base (7).

18. An interdental cleaning device according to claim 17, wherein knob-type legs (8) are disposed on the base (7).

19. An interdental cleaning device according to claim 14, wherein a recessed grip (10, 11) is formed away from an inner edge on at least one of the two shells (2, 3).

* * * * *